(12) United States Patent
Chen et al.

(10) Patent No.: US 11,773,367 B2
(45) Date of Patent: Oct. 3, 2023

(54) METHOD OF ENHANCING CONTINUOUS DIRECTIONAL HIGH-VALUE BIOLOGICAL CONVERSION OF URBAN WET GARBAGE OPEN SYSTEM

(71) Applicants: Tongji University, Shanghai (CN); Jiangnan University, Shanghai (CN)

(72) Inventors: Yinguang Chen, Shanghai (CN); Xiong Zheng, Shanghai (CN); Xuemeng Zhang, Shanghai (CN); Jing Zhou, Shanghai (CN); Meirou Wu, Shanghai (CN); Chen Wang, Shanghai (CN); Wenquan Ruan, Shanghai (CN); Hengfeng Miao, Shanghai (CN); Mingxing Zhao, Shanghai (CN)

(73) Assignee: TONGJI UNIVERSITY, Shanghai (CN)

( * ) Notice: Subject to any disclaimer, the term of this patent is extended or adjusted under 35 U.S.C. 154(b) by 0 days.

(21) Appl. No.: 17/475,182

(22) Filed: Sep. 14, 2021

(65) Prior Publication Data

US 2023/0027602 A1     Jan. 26, 2023

(30) Foreign Application Priority Data

Jul. 21, 2021    (CN) .......................... 202110299759.4

(51) Int. Cl.
*C12N 1/36*        (2006.01)
*C12P 7/52*        (2006.01)
*C12P 7/54*        (2006.01)

(52) U.S. Cl.
CPC ................. *C12N 1/36* (2013.01); *C12P 7/52* (2013.01); *C12P 7/54* (2013.01)

(58) Field of Classification Search
CPC ................. C12N 1/36; C12P 7/52; C12P 7/54
See application file for complete search history.

(56) References Cited

U.S. PATENT DOCUMENTS

| | | | |
|---|---|---|---|
| 2015/0191754 A1* | 7/2015 | Chen ........................ | C12P 7/40 435/141 |
| 2018/0044213 A1* | 2/2018 | Chen ........................ | C02F 9/00 |

OTHER PUBLICATIONS

Zhu G et al. Flow Simulation and Analysis in a Vertical-Flow Sedimentation Tank. 2012. Energy Procedia 16. 197-202 (Year: 2012).*

* cited by examiner

*Primary Examiner* — Paul J Holland
(74) *Attorney, Agent, or Firm* — Locke Lord LLP; Tim Tingkang Xia, Esq.

(57) ABSTRACT

The present invention provides a method of enhancing continuous directional high-value biological conversion of an urban wet garbage open system. The method includes wet garbage crushing, low-energy consumption hydrolysis, continuous conversion of organic components of wet garbage into short-chain fatty acid, continuous directional conversion of other components of short-chain fatty acid into acetic acid, separation and microbial reflux of acetic acid, and the like. In this method, by crushing wet garbage, performing low-energy consumption hydrolysis, and seeding acclimatized activated sludge, two stages of anaerobic fermentations are carried out to firstly convert organic components of the wet garbage continuously into short-chain fatty acid, and then continuously and directionally convert other components of short-chain fatty acid into acetic acid, so as to realize continuous directional high-value biological conversion of the urban wet garbage in an open system without adding pure microbes and a large amount of chemicals.

10 Claims, 2 Drawing Sheets

METHOD OF ENHANCING CONTINUOUS DIRECTIONAL HIGH-VALUE BIOLOGICAL CONVERSION OF URBAN WET GARBAGE OPEN SYSTEM

CROSS-REFERENCE TO RELATED APPLICATION

This application claims priority from the Chinese patent application 2021102997594 filed Jul. 21, 2021, the content of which are incorporated herein in the entirety by reference.

TECHNICAL FIELD

The present invention relates to the field of environmental protection technologies and in particular to a method of enhancing continuous directional high-value biological conversion of an urban wet garbage open system.

BACKGROUND

Along with rapid economic and urban development, a total amount of urban domestic garbage tends to increase yearly. Thus, a prominent research topic relates to converting such waste into useful products so as to realize a resource-oriented utilization of the waste. Due to high water content, low calorific value and perishability of wet garbage, conventional resource utilization approaches, such as incineration power generation, are not suitable for the wet garbage in spite of a large amount of organic matter contained therein. Therefore, it is an urgent problem for researchers to effectively dispose of wet garbage based on resource-oriented utilization and promote social benefits, economic benefits and environmental benefits.

Generation of methane by anaerobic digestion of wet garbage is currently one way to realize resource-oriented utilization of wet garbage. In this process, organic matter such as polysaccharides and proteins are converted into gases such as methane, carbon dioxide, and hydrogen under the action of hydrolases, acid-producing microbes and methanogenic bacteria. Another resource-oriented utilization method for wet garbage is high-temperature aerobic composting. In this method, obligate and facultative aerobic bacteria enable microbes to multiply and degrade organic matters to stabilization with appropriate moisture and ventilation. By applying these methods, the disposal of wet garbage after classification of garbage is relieved to some extent. To further improve resource-oriented utilization of wet garbage in converting organic matters contained therein into products of higher value, a new approach is provided.

It is well known that in contrast with a closed aseptic operation system or a system where pure microbes are present, the organic matter may generate a given amount of short-chain fatty acid of propanoic acid (SCFA, including acetic acid, propanoic acid, butyric acid and lactic acid) due to presence of multiple types of microbes in the system when performing anaerobic conversion in an open system. SCFA is only an intermediate and will not accumulate in large amounts. In order to improve the high-value utilization level of wet garbage, pure microbes (e.g. acetic acid bacteria), fermentation agents, surfactants or a large amount of other chemicals (as described in CN201410073745.0, CN201610107225.6, CN201910362210.8 and CN201910721054.X and the like) may be added. Although production of SCFA can be increased using these methods, use of pure microbes or a large amount of chemicals increases production costs or secondary pollution of the environment. Furthermore, batch production and operation is difficult to implement.

SUMMARY

In order to solve the drawbacks of the prior art, the object of the present invention is to provide a method of enhancing continuous directional high-value biological conversion of an urban wet garbage open system. In this method, by crushing wet garbage, performing low-energy consumption hydrolysis, and seeding acclimatized activated sludge microbes, two stages of anaerobic fermentations are carried out to firstly convert organic components of the wet garbage continuously into short-chain fatty acid, and then continuously and directionally convert other components of short-chain fatty acid into acetic acid, so as to realize continuous directional high-value biological conversion of the urban wet garbage in an open system without adding pure microbes and a large amount of chemicals.

The present invention provides the following technical solution: a method of enhancing continuous directional high-value biological conversion of an urban wet garbage open system, which comprises the following steps:

(1) wet garbage crushing: crushing a wet garbage and then adding tap water to perform cooking and oil extraction, and then pumping a water phase of the crushed wet garbage into a hydrolysis reactor H;

(2) low-energy consumption hydrolysis: hydrolyzing the water phase of the crushed wet garbage in the hydrolysis reactor H to obtain a hydrolysate and then pumping the obtained hydrolysate into a storage tank S1;

(3) microbial acclimation of an activated sludge for converting organic components of the wet garbage into short-chain fatty acid: adding an urban sewage into a microbial acclimation reactor A1, and then adding a wastewater plant residual sludge and the hydrolysate respectively to enable a starting sludge concentration to be 8000 mg/L and a starting hydrolysate COD to be 1000 mg/L in the microbial acclimation reactor A1, adjusting a pH of the mixture in the microbial acclimation reactor A1 to 8, and performing anaerobic stirring and acclimation for the mixture at a temperature of 25° C.; when a total amount of short-chain fatty acid in the reactor does not change obviously any longer over time, taking the sludge as a seeding sludge for converting organic components of the wet garbage into short-chain fatty acid (SCFA) efficiently;

(4) continuous conversion of organic components of the wet garbage into short-chain fatty acid: pumping the hydrolysate in the storage tank S1 and 500 mL of the seeding sludge acclimatized at step (3) into an SCFA-producing reactor R1 to enable a sludge concentration in the SCFA-producing reactor R1 to be 2000 mg/L and controlling a temperature, a pH value, a hydraulic retention time, and a microbial retention time to fully convert the organic components of the wet garbage into a mixture rich in short-chain fatty acid;

(5) separation and microbial reflux of short-chain fatty acid: introducing the generated mixture rich in short-chain fatty acid into a settling tank C1 for solid-liquid separation, introducing a supernatant obtained through solid-liquid separation into a storage tank S2, and refluxing a part of a precipitate obtained through solid-liquid separation to the SCFA-producing reactor R1;

(6) microbial acclimation of an activated sludge for directional conversion of other components of short-chain fatty acid into acetic acid: adding urban sewage, a wastewater plant residual sludge and the liquid in the storage tank S2 to another microbial acclimation reactor A2 to enable a sludge concentration to be 8600 mg/L and a short-chain fatty acid COD to be 1000 mg/L in the microbial acclimation reactor A2, adjusting a pH to 9, and performing anaerobic stirring and acclimation at a temperature of 25° C. to enable propanoic acid, butyric acid and pentanoic acid in the short-chain fatty acid obtained by converting the wet garbage to be directionally converted into acetic acid;

(7) continuous directional conversion of other components of short-chain fatty acid into acetic acid: pumping the liquid in the storage tank S2 and 800 ml of the sludge acclimatized at step (6) to a reactor R2 for converting other components of SCFA into acetic acid to enable a sludge concentration to be 9000 mg/L in the reactor R2 for converting other components into acetic acid, and controlling a temperature, a pH value, a hydraulic retention time, and a microbial retention time to enable propanoic acid, butyric acid and pentanoic acid in the SCFA produced at step (4) to be directionally converted into acetic acid;

(8) acetic acid separation and microbial reflux: introducing an acetic acid-rich mixture produced by the reactor R2 for converting other components of SCFA into acetic acid into a settling tank C2 for solid-liquid separation, obtaining a supernatant as an acetic acid-rich liquid through solid-liquid separation and refluxing a part of a precipitate obtained through solid-liquid separation to the reactor R2.

Furthermore, a molar ratio of carbon to nitrogen of the wet garbage is 18-35:1, and a particle size of the crushed wet garbage is 0.05-2 mm.

Furthermore, working conditions of the hydrolysis reactor H are temperature 20-100° C., pH value 3-12 and time 5-120 hours.

Furthermore, the working conditions of the hydrolysis reactor H are temperature 40° C., pH value 11 and time 60 hours.

Furthermore, conditions for continuously converting the organic components of the wet garbage into short-chain fatty acid at step (4) are: temperature 10-70° C., pH value 5-10, hydraulic retention time 1-8 days, microbial mean retention time 3-10 days.

Furthermore, the conditions for continuously converting the organic components of the wet garbage into short-chain fatty acid at step (4) are: temperature 25° C., pH value 8, hydraulic retention time 5 days, microbial mean retention time 6 days.

Furthermore, the settling tank C1 is a vertical flow settling tank with a depth-diameter ratio of 2.5 and a round hopper tilt angle of 55 degrees, and a microbial reflux amount at step (5) is 0-60% of an inlet water amount of the SCFA-producing reactor R1.

Furthermore, conditions for continuous directional conversion of other components of short-chain fatty acid into acetic acid at step (6) are: temperature 10-80° C., pH value 4-12, hydraulic retention time 0.5-6 days, microbial mean retention time 1-13 days.

Furthermore, the conditions for continuous directional conversion of other components of short-chain fatty acid into acetic acid at step (6) are: temperature 25° C., pH value 9, hydraulic retention time 3 days, microbial mean retention time 8 days.

Furthermore, the settling tank C2 is a vertical flow settling tank with a depth-diameter ratio of 3 and a round hopper tilt angle of 60 degrees, and a microbial reflux amount at step (8) is 0-100% of an inlet water amount of the reactor R2 for converting other components of SCFA into acetic acid.

The present invention has the following beneficial effects:

In the method of enhancing continuous directional high-value biological conversion of an urban wet garbage open system, operations such as crushing wet garbage, low-energy consumption hydrolysis, continuous conversion of organic components of the wet garbage into short-chain fatty acid, continuous directional conversion of other components of short-chain fatty acid into acetic acid, acetic acid separation and microbial reflux and the like are carried out to realize continuous directional high-value biological conversion of the urban wet garbage in an open system without adding pure microbes and a large amount of chemicals, which provides a new thought for efficient disposal and high-value directional conversion of the wet garbage.

BRIEF DESCRIPTIONS OF THE DRAWINGS

The present invention will be further detailed below in combination with specific embodiments and accompanying drawings.

DETAILED DESCRIPTIONS OF EMBODIMENTS

Figure 1:
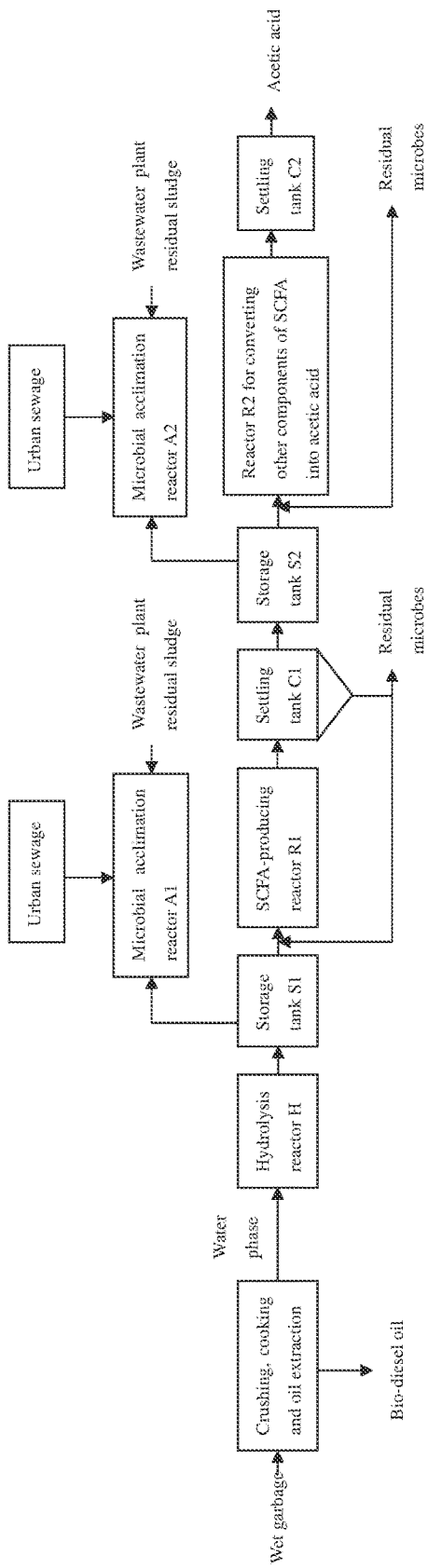
FIG. 1 is a flowchart of a method of enhancing continuous directional high-value biological conversion of an urban wet garbage open system according to an embodiment of the present invention.

The implementations of the present invention will be described by specific embodiments. Those skilled in the art may easily understand other advantages and efficacies of the present invention from the contents disclosed in the specification. The present invention may also be practiced or applied by other different specific implementations. Various details of the specification may be modified or changed based on different viewpoints and applications without departing from the spirit of the present invention. It is noted that the following embodiments and features of the following embodiments may be combined with each other in a case of no conflicts. It should also be understood that the terms used in the embodiments of the present invention are used for describing a particular implementation solution rather than limiting the scope of protection of the present invention. Those test methods without specific conditions in the following embodiments are usually carried out under normal conditions or under the conditions recommended by various manufacturers.

It should be understood that, when a value range is given in an embodiment, two endpoints of the value range and any value between the two endpoints may be selected unless otherwise stated. Unless otherwise defined, in addition to all technical and scientific terms used in the present invention and the understandings of the prior art made by those skilled in the art and recordings of the present invention, any method, apparatus and material of the prior art similar to or equivalent to the method, apparatus and material of the embodiments of the present invention may also be used to carry out the present invention.

Embodiment 1

Microbial acclimation of an activated sludge for converting organic components of wet garbage into short-chain fatty acid (SCFA): a wet garbage with a molar ratio of carbon to nitrogen being (18-35):1 was crushed at room temperature (a particle size was (0.05-2) mm) and then added to a hydrolysis reactor H and hydrolyzed for 60 hours at a temperature of 40° C. and a pH value of 11 to obtain a hydrolysate. Next, an urban sewage (COD 138-183 mg/L) was added to a microbial acclimation reactor A1 and a wastewater plant residual sludge and the hydrolysate were then added to the microbial acclimation reactor A1 to enable a starting sludge concentration and a starting hydrolysate COD to be 8000 mg/L and 1000 mg/L, respectively. In the microbial acclimation reactor A1, a pH value of the mixture in the reactor was adjusted to 8 and anaerobic stirring was performed for the mixture at a temperature of 25° C. In the first to tenth days of the acclimation, hydrolysate COD 1000 mg/L was replenished each day with no sludge being discharged and only supernatant being discharged to maintain an unchanged total volume. In the eleventh to twentieth days of the acclimation, hydrolysate COD 2000 mg/L was replenished each day to maintain a microbial mean retention time of 6 days and an unchanged total volume From the twenty-first day on, hydrolysate COD 4000 mg/L was replenished each day to maintain a microbial mean retention time of 6 days and an unchanged total volume. After acclimation of 43 days, a total amount of short-chain fatty acid in the reactor will no longer change obviously over time, and the sludge was taken as a seeding sludge for efficiently converting organic components of the wet garbage into SCFA.

Microbial acclimation of an activated sludge for directional conversion of other components of SCFA into acetic acid: the above hydrolysate and 500 mL of acclimatized seeding sludge were added to a short-chain fatty acid-producing reactor to enable a sludge concentration of 2000 mg/L, stirred for 5 days at a temperature of 25° C. and a pH value of 8, and then centrifuged for separation to obtain a supernatant as a short-chain fatty acid-rich liquid. Next, an urban sewage (COD 138-183 mg/L), a wastewater plant residual sludge, and the short-chain fatty acid-rich mixture were added to another microbial acclimation reactor A2 resulting in a sludge concentration of 8600 mg/L and a short-chain fatty acid COD of 1000 mg/L, a pH value was adjusted to 9, and anaerobic stirring and acclimation were performed at a temperature of 25° C. In the first to twelfth days of the acclimation, the short-chain fatty acid-rich liquid COD 800 mg/L was replenished each day with no sludge being discharged and only supernatant being discharged to maintain an unchanged total volume. In the thirteenth to twenty-second days of the acclimation, the short-chain fatty acid-rich liquid COD 2000 mg/L was replenished each day to maintain a microbial mean retention time of 8 days and an unchanged total volume. From the twenty-third day on, the short-chain fatty acid-rich liquid (COD 3000 mg/L) was replenished each day to maintain a microbial mean retention time of 8 days and an unchanged total volume. After acclimation of 35 days, a content of acetic acid in the reactor will no longer change obviously over time, and the sludge was taken as a seeding sludge for directionally converting other components of the SCFA into acetic acid.

Figure 2:
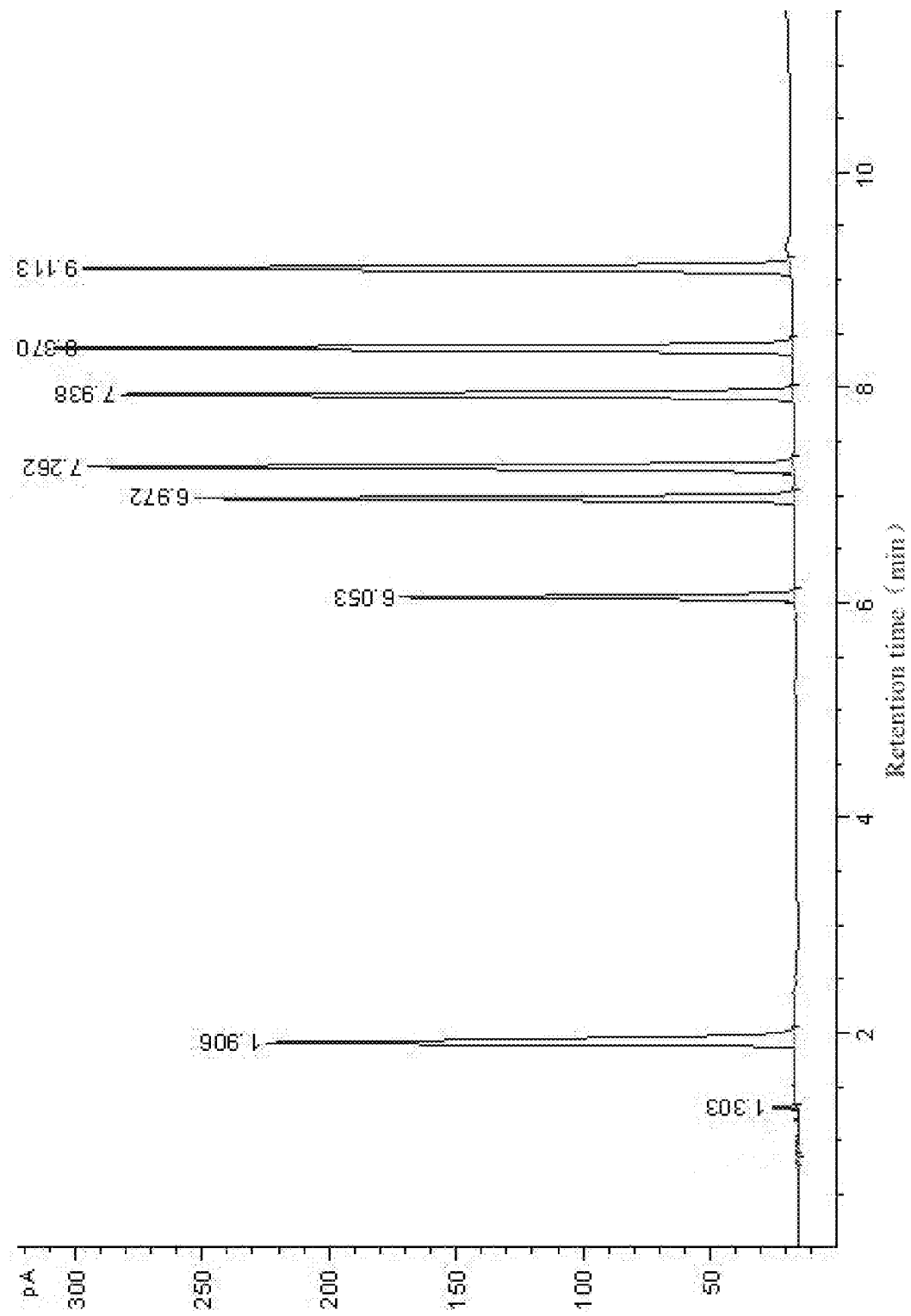
FIG. 2 is a standard diagram of major ingredients of a final supernatant according to a first embodiment of the present invention.

Continuous directional high-value biological conversion of the urban wet garbage open system: the wet garbage with a molar ratio of carbon to nitrogen being (18-35):1 was crushed at room temperature (a particle size (0.05-2) mm) and then subjected to cooking and oil extraction, and a water phase was pumped into a hydrolysis reactor H with a temperature of 20° C., a pH value of 3 and a hydrolysis time of 5 hours; a hydrolyzed liquid was placed in a storage tank S1, and then transported through a pump to an SCFA-producing reactor R1 with a temperature of 10° C., a pH value of 5, a hydraulic retention time of 1 day, and a microbial retention time of 3 days; a supernatant was obtained through solid-liquid separation of a settling tank C1, placed in a storage tank S2, and transported through a pump to a reactor R2 for directionally converting other components of SCFA into acetic acid (wherein operation conditions were a temperature of 10° C., a pH of 4, a hydraulic retention time of 0.5 days, and a microbial retention time of 1 day); an effluent of the R2 was subjected to solid-liquid separation of a settling tank C2 to obtain a final supernatant as an acetic acid-rich liquid. According to analysis of the Agilent 6890 type gas chromatograph and a peak time of a standard sample, acetic acid concentrations of the supernatants of the settling tanks C1 and C2 were obtained as 1031 mg/L and 2614 mg/L, respectively. The gas chromatograph analyzes acetic acid by the following method: before determination, a sample was firstly filtered in a high-speed centrifuge at a speed of 16000 r/min, and then press-filtered using a filtration membrane of 0.45 μm, with a filtrate collected into a 1.5 mL gas chromatography-specific brown vial, and then 3% $H_3PO_4$ was added to the vial to ensure a pH value of the sample was smaller than 5; a chromatographic column model was utilized (DB-WAXETR, 30 m×1.0 μm×0.53 mm); a flow rate of a carrier gas ($N_2$) was 25 mL/min; a detector was a hydrogen flame ionization detector (FID); a temperature of a vaporization chamber was 220° C.; a temperature of the FID was 250° C.; under a temperature increase program, a starting furnace temperature was 60° C. and ran for 1 minute, increased to 100° C. at the speed of 20° C./min and ran for 1 minute, and increased to 180° C. at the speed of 10° C./min and ran for 1 minute. An entire running time of one sample was about 13 minutes with each load amount being 1.0 μL. FIG. 2 is a standard diagram of major ingredients in a final supernatant, where those with peak times being about 2 minutes were impurity peaks; those with peak times being about 1.9 min, 6.1 min, 6.9 min, 7.3 min, 7.9 min, 8.4 min and 9 min respectively were ethanol, acetic acid, propanoic acid, isobutyric acid, n-butyric acid, isopentanoic acid, and n-pentanoic acid sequentially. The concentration of acetic acid can be calculated according to a relationship between a concentration of standard sample of acetic acid and a peak area at the time of a peak time of 6.1 min.

Embodiment 2

The methods for microbial acclimation of an activated sludge for conversion of organic components of the wet garbage into short-chain fatty acid (SCFA), microbial acclimation of an activated sludge for directional conversion of other components of the SCFA into acetic acid, and analysis of the gas chromatograph for acetic acid are similar to embodiment 1. The method for continuous directional high-value biological conversion of the urban wet garbage open system is as follows: the wet garbage with a molar ratio of carbon to nitrogen being (18-35):1 was crushed at room temperature (a particle size (0.05-2) mm) and then subjected to cooking and oil extraction, and a water phase was pumped into the hydrolysis reactor H with a temperature of 20° C., a pH value of 3 and a hydrolysis time of 5 hours; a hydrolyzed liquid was placed in the storage tank S1, and then transported through a pump to the SCFA-producing reactor R1 with a temperature of 10° C., a pH value of 5, a hydraulic retention time of 1 day, and a microbial retention time of 3 days; after solid-liquid separation of the settling tank C1, a microbial reflux amount of a precipitate was 20% of an inlet water amount of R1, a supernatant was placed in the storage tank S2 and then transported through a pump to the reactor R2 for directionally converting other components of SCFA into acetic acid (where operation conditions were a temperature of 10° C., a pH of 4, a hydraulic retention time of 0.5 days, and a microbial retention time of 1 day); an effluent of the R2 was subjected to solid-liquid separation of the settling tank C2, a microbial reflux amount of a precipitate was 20% of an inlet water amount of the R2, and a final supernatant was obtained as an acetic acid-rich liquid. According to analysis of the Agilent 6890 type gas chromatograph and a peak time of a standard sample, acetic acid concentrations of the supernatants of the settling tanks C1 and C2 were obtained as 1924 mg/L and 3423 mg/L, respectively.

Embodiment 3

The methods for microbial acclimation of an activated sludge for conversion of organic components of the wet garbage into short-chain fatty acid (SCFA), microbial acclimation of an activated sludge for directional conversion of other components of the SCFA into acetic acid, and analysis of the gas chromatograph for acetic acid are similar to embodiment 1. The method for continuous directional high-value biological conversion of the urban wet garbage open system is as follows: the wet garbage with a molar ratio of carbon to nitrogen being (18-35):1 was crushed at room temperature (a particle size (0.05-2) mm) and subjected to cooking and oil extraction, and a water phase was pumped into the hydrolysis reactor H with a temperature of 30° C., a pH value of 4 and a hydrolysis time of 12 hours; a hydrolyzed liquid was placed in the storage tank S1, and then transported through a pump to the SCFA-producing reactor R1 with a temperature of 20° C., a pH value of 6, a hydraulic retention time of 2 days, and a microbial retention time of 4 days; after solid-liquid separation of the settling tank C1, a microbial reflux amount of a precipitate was 20% of an inlet water amount of R1, a supernatant was placed in the storage tank S2 and then transported through a pump to the reactor R2 for directionally converting other components of SCFA into acetic acid (where operation conditions were a temperature of 20° C., a pH of 5, a hydraulic retention time of 1 day, and a microbial retention time of 2 days); an effluent of the R2 was subjected to solid-liquid separation of the settling tank C2, a microbial reflux amount of a precipitate was 30% of an inlet water amount of the R2, and a final supernatant was obtained as an acetic acid-rich liquid. According to analysis of the Agilent 6890 type gas chromatograph and a peak time of a standard sample, acetic acid concentrations of the supernatants of the settling tanks C1 and C2 were obtained as 2012 mg/L and 3697 mg/L, respectively.

Embodiment 4

The methods for microbial acclimation of an activated sludge for conversion of organic components of the wet garbage into short-chain fatty acid (SCFA), microbial acclimation of an activated sludge for directional conversion of other components of the SCFA into acetic acid, and analysis of the gas chromatograph for acetic acid are similar to embodiment 1. The method for continuous directional high-value biological conversion of the urban wet garbage open system is as follows: the wet garbage with a molar ratio of carbon to nitrogen being (18-35):1 was crushed at room temperature (a particle size (0.05-2) mm) and subjected to cooking and oil extraction, and a water phase was pumped into the hydrolysis reactor H with a temperature of 30° C., a pH value of 5 and a hydrolysis time of 18 hours; a hydrolyzed liquid was placed in the storage tank S1, and then transported through a pump to the SCFA-producing reactor R1 with a temperature of 25° C., a pH value of 7, a hydraulic retention time of 2 days, and a microbial retention time of 4 days; after solid-liquid separation of the settling tank C1, a microbial reflux amount of a precipitate was 20% of an inlet water amount of R1, a supernatant was placed in the storage tank S2 and then transported through a pump to the reactor R2 for directionally converting other components of SCFA into acetic acid (where operation conditions were a temperature of 20° C., a pH of 5, a hydraulic retention time of 1 day, and a microbial retention time of 2.5 days); an effluent of the R2 was subjected to solid-liquid separation of the settling tank C2, a microbial reflux amount of a precipitate was 20% of an inlet water amount of the R2, and a final supernatant was obtained as an acetic acid-rich liquid. According to analysis of the Agilent 6890 type gas chromatograph and a peak time of a standard sample, acetic acid concentrations of the supernatants of the settling tanks C1 and C2 were obtained as 1987 mg/L and 3904 mg/L, respectively.

Embodiment 5

The methods for microbial acclimation of an activated sludge for conversion of organic components of the wet garbage into short-chain fatty acid (SCFA), microbial acclimation of an activated sludge for directional conversion of other components of the SCFA into acetic acid, and analysis of the gas chromatograph for acetic acid are similar to embodiment 1. The method for continuous directional high-value biological conversion of the urban wet garbage open system is as follows: the wet garbage with a molar ratio of carbon to nitrogen being (18-35):1 was crushed at room temperature (a particle size (0.05-2) mm) and subjected to cooking and oil extraction, and a water phase was pumped into the hydrolysis reactor H with a temperature of 40° C., a pH value of 6 and a hydrolysis time of 24 hours; a hydrolyzed liquid was placed in the storage tank S1, and then transported through a pump to the SCFA-producing reactor R1 with a temperature of 35° C., a pH value of 7, a hydraulic retention time of 3 days, and a microbial retention time of 4 days; after solid-liquid separation of the settling tank C1, a microbial reflux amount of a precipitate was 20% of an inlet water amount of R1, a supernatant was placed in the storage tank S2 and then transported through a pump to the reactor R2 for directionally converting other components of SCFA into acetic acid (where operation conditions were a temperature of 25° C., a pH of 6, a hydraulic retention time of 2 days, and a microbial retention time of 3 days); an effluent of the R2 was subjected to solid-liquid separation of the settling tank C2, a microbial reflux amount of a precipitate was 40% of an inlet water amount of the R2, and a final supernatant was obtained as an acetic acid-rich liquid. According to analysis of the Agilent 6890 type gas chromatograph and a peak time of a standard sample, acetic acid concentrations of the supernatants of the settling tanks C1 and C2 were obtained as 2546 mg/L and 4429 mg/L, respectively.

Embodiment 6

The methods for microbial acclimation of an activated sludge for conversion of organic components of the wet garbage into short-chain fatty acid (SCFA), microbial acclimation of an activated sludge for directional conversion of other components of the SCFA into acetic acid, and analysis of the gas chromatograph for acetic acid are similar to embodiment 1. The method for continuous directional high-value biological conversion of the urban wet garbage open system is as follows: the wet garbage with a molar ratio of carbon to nitrogen being (18-35):1 was crushed at room temperature (a particle size (0.05-2) mm) and subjected to cooking and oil extraction, and a water phase was pumped into the hydrolysis reactor H with a temperature of 60° C., a pH value of 7 and a hydrolysis time of 30 hours; a hydrolyzed liquid was placed in the storage tank S1, and then transported through a pump to the SCFA-producing reactor R1 with a temperature of 10° C., a pH value of 8, a hydraulic retention time of 4 days, and a microbial retention time of 5 days; after solid-liquid separation of the settling tank C1, a microbial reflux amount of a precipitate was 20% of an inlet water amount of R1, a supernatant was placed in the storage tank S2 and then transported through a pump to the reactor R2 for directionally converting other components of SCFA into acetic acid (where operation conditions were a temperature of 40° C., a pH of 7, a hydraulic retention time of 3 days, and a microbial retention time of 3 days); an effluent of the R2 was subjected to solid-liquid separation of the settling tank C2, a microbial reflux amount of a precipitate was 20% of an inlet water amount of the R2, and a final supernatant was obtained as an acetic acid-rich liquid. According to analysis of the Agilent 6890 type gas chromatograph, an acetic acid concentration of the supernatant of the settling tank C2 was obtained as 3765 mg/L.

Embodiment 7

The methods for microbial acclimation of an activated sludge for conversion of organic components of the wet garbage into short-chain fatty acid (SCFA), microbial acclimation of an activated sludge for directional conversion of other components of the SCFA into acetic acid, and analysis of the gas chromatograph for acetic acid are similar to embodiment 1. The method for continuous directional high-value biological conversion of the urban wet garbage open system is as follows: the wet garbage with a molar ratio of carbon to nitrogen being (18-35):1 was crushed at room temperature (a particle size (0.05-2) mm) and subjected to cooking and oil extraction, and a water phase was pumped into the hydrolysis reactor H with a temperature of 80° C., a pH value of 8 and a hydrolysis time of 36 hours; a hydrolyzed liquid was placed in the storage tank S1, and then transported through a pump to the SCFA-producing reactor R1 with a temperature of 50° C., a pH value of 8, a hydraulic retention time of 5 days, and a microbial retention time of 6 days; after solid-liquid separation of the settling tank C1, a microbial reflux amount of a precipitate was 20% of an inlet water amount of R1, a supernatant was placed in the storage tank S2 and then transported through a pump to the reactor R2 for directionally converting other components of SCFA into acetic acid (where operation conditions were a temperature of 50° C., a pH of 8, a hydraulic retention time of 4 days, and a microbial retention time of 4 days); an effluent of the R2 was subjected to solid-liquid separation of the settling tank C2, a microbial reflux amount of a precipitate was 60% of an inlet water amount of the R2, and a final supernatant was obtained as an acetic acid-rich liquid. According to analysis of the Agilent 6890 type gas chromatograph, an acetic acid concentration of the supernatant of the settling tank C2 was obtained as 4667 mg/L.

Embodiment 8

The methods for microbial acclimation of an activated sludge for conversion of organic components of the wet garbage into short-chain fatty acid (SCFA), microbial acclimation of an activated sludge for directional conversion of other components of the SCFA into acetic acid, and analysis of the gas chromatograph for acetic acid are similar to embodiment 1. The method for continuous directional high-value biological conversion of the urban wet garbage open system is as follows: the wet garbage with a molar ratio of carbon to nitrogen being (18-35):1 was crushed at room temperature (a particle size (0.05-2) mm) and subjected to cooking and oil extraction, and a water phase was pumped into the hydrolysis reactor H with a temperature of 90° C., a pH value of 11 and a hydrolysis time of 48 hours; a hydrolyzed liquid was placed in the storage tank S1, and then transported through a pump to the SCFA-producing reactor R1 with a temperature of 60° C., a pH value of 9, a hydraulic retention time of 7 days, and a microbial retention time of 8 days; after solid-liquid separation of the settling tank C1, a microbial reflux amount of a precipitate was 20% of an inlet water amount of R1, a supernatant was placed in the storage tank S2 and then transported through a pump to the reactor R2 for directionally converting other components of SCFA into acetic acid (where operation conditions were a temperature of 60° C., a pH of 9, a hydraulic retention time of 5 days, and a microbial retention time of 8 days); an effluent of the R2 was subjected to solid-liquid separation of the settling tank C2, a microbial reflux amount of a precipitate was 45% of an inlet water amount of the R2, and a final supernatant was obtained as an acetic acid-rich liquid. According to analysis of the Agilent 6890 type gas chromatograph, an acetic acid concentration of the supernatant of the settling tank C2 was obtained as 4825 mg/L.

Embodiment 9

The methods for microbial acclimation of an activated sludge for conversion of organic components of the wet garbage into short-chain fatty acid (SCFA), microbial acclimation of an activated sludge for directional conversion of other components of the SCFA into acetic acid, and analysis of the gas chromatograph for acetic acid are similar to embodiment 1. The method for continuous directional high-value biological conversion of the urban wet garbage open system is as follows: the wet garbage with a molar ratio of carbon to nitrogen being (18-35):1 was crushed at room temperature (a particle size (0.05-2) mm) and subjected to cooking and oil extraction, and a water phase was pumped into the hydrolysis reactor H with a temperature of 100° C., a pH value of 12 and a hydrolysis time of 60 hours; a hydrolyzed liquid was placed in the storage tank S1, and then transported through a pump to the SCFA-producing reactor R1 with a temperature of 70° C., a pH value of 10, a hydraulic retention time of 8 days, and a microbial retention time of 10 days; after solid-liquid separation of the settling tank C1, a microbial reflux amount of a precipitate was 20% of an inlet water amount of R1, a supernatant was placed in the storage tank S2 and then transported through a pump to the reactor R2 for directionally converting other components of SCFA into acetic acid (where operation conditions were a temperature of 20° C., a pH of 12, a hydraulic retention time of 6 days, and a microbial retention time of 3 days); an effluent of the R2 was subjected to solid-liquid separation of the settling tank C2, a microbial reflux amount of a precipitate was 80% of an inlet water amount of the R2, and a final supernatant was obtained as an acetic acid-rich liquid. According to analysis of the Agilent 6890 type gas chromatograph, an acetic acid concentration of the supernatant of the settling tank C2 was obtained as 4129 mg/L.

Embodiment 10

The methods for microbial acclimation of an activated sludge for conversion of organic components of the wet garbage into short-chain fatty acid (SCFA), microbial acclimation of an activated sludge for directional conversion of other components of the SCFA into acetic acid, and analysis of the gas chromatograph for acetic acid are similar to embodiment 1. The method for continuous directional high-value biological conversion of the urban wet garbage open system is as follows: the wet garbage with a molar ratio of carbon to nitrogen being (18-35):1 was crushed at room temperature (a particle size (0.05-2) mm) and subjected to cooking and oil extraction, and a water phase was pumped into the hydrolysis reactor H with a temperature of 30° C., a pH value of 9 and a hydrolysis time of 120 hours; a hydrolyzed liquid was placed in the storage tank S1, and then transported through a pump to the SCFA-producing reactor R1 with a temperature of 40° C., a pH value of 7, a hydraulic retention time of 5 days, and a microbial retention time of 4 days; after solid-liquid separation of the settling tank C1, a microbial reflux amount of a precipitate was 20% of an inlet water amount of R1, a supernatant was placed in the storage tank S2 and then transported through a pump to the reactor R2 for directionally converting other components of SCFA into acetic acid (where operation conditions were a temperature of 80° C., a pH of 6, a hydraulic retention time of 3 days, and a microbial retention time of 13 days); an effluent of the R2 was subjected to solid-liquid separation of the settling tank C2, a microbial reflux amount of a precipitate was 100% of an inlet water amount of the R2, and a final supernatant was obtained as an acetic acid-rich liquid. According to analysis of the Agilent 6890 type gas chromatograph, an acetic acid concentration of the supernatant of the settling tank C2 was obtained as 4315 mg/L.

Embodiment 11

The methods for microbial acclimation of an activated sludge for conversion of organic components of the wet garbage into short-chain fatty acid (SCFA), microbial acclimation of an activated sludge for directional conversion of other components of the SCFA into acetic acid, and analysis of the gas chromatograph for acetic acid are similar to embodiment 1. The method for continuous directional high-value biological conversion of the urban wet garbage open system is as follows: the wet garbage with a molar ratio of carbon to nitrogen being (18-35):1 was crushed at room temperature (a particle size (0.05-2) mm) and subjected to cooking and oil extraction, and a water phase was pumped into the hydrolysis reactor H with a temperature of 40° C., a pH value of 11 and a hydrolysis time of 60 hours; a hydrolyzed liquid was placed in the storage tank S1, and then transported through a pump to the SCFA-producing reactor R1 with a temperature of 25° C., a pH value of 8, a hydraulic retention time of 5 days, and a microbial retention time of 6 days; after solid-liquid separation of the settling tank C1, a microbial reflux amount of a precipitate was 20% of an inlet water amount of R1, a supernatant was placed in the storage tank S2 and then transported through a pump to the reactor R2 for directionally converting other components of SCFA into acetic acid (where operation conditions were a temperature of 25° C., a pH of 9, a hydraulic retention time of 3 days, and a microbial retention time of 8 days); an effluent of the R2 was subjected to solid-liquid separation of the settling tank C2, a microbial reflux amount of a precipitate was 50% of an inlet water amount of the R2, and a final supernatant was obtained as an acetic acid-rich liquid. According to analysis of the Agilent 6890 type gas chromatograph, an acetic acid concentration of the supernatant of the settling tank C2 was obtained as 5172 mg/L.

Embodiment 12

The methods for microbial acclimation of an activated sludge for conversion of organic components of the wet garbage into short-chain fatty acid (SCFA), microbial acclimation of an activated sludge for directional conversion of other components of the SCFA into acetic acid, and analysis of the gas chromatograph for acetic acid are similar to embodiment 1. The method for continuous directional high-value biological conversion of the urban wet garbage open system is as follows: the wet garbage with a molar ratio of carbon to nitrogen being (18-35):1 was crushed at room temperature (a particle size (0.05-2) mm) and subjected to cooking and oil extraction, and a water phase was pumped into the hydrolysis reactor H with a temperature of 20° C., a pH value of 3 and a hydrolysis time of 5 hours; a hydrolyzed liquid was placed in the storage tank S1, and then transported through a pump to the SCFA-producing reactor R1 with a temperature of 10° C., a pH value of 5, a hydraulic retention time of 1 day, and a microbial retention time of 3 days; after solid-liquid separation of the settling tank C1, a microbial reflux amount of a precipitate was 40% of an inlet water amount of R1, a supernatant was placed in the storage tank S2 and then transported through a pump to the reactor R2 for directionally converting other components of SCFA into acetic acid (where operation conditions were a temperature of 10° C., a pH of 4, a hydraulic retention time of 0.5 days, and a microbial retention time of 1 day); an effluent of the R2 was subjected to solid-liquid separation of the settling tank C2, a microbial reflux amount of a precipitate was 20% of an inlet water amount of the R2, and a final supernatant was obtained as an acetic acid-rich liquid. According to analysis of the Agilent 6890 type gas chromatograph, an acetic acid concentration of the supernatant of the settling tank C2 was obtained as 3648 mg/L.

Embodiment 13

The methods for microbial acclimation of an activated sludge for conversion of organic components of the wet garbage into short-chain fatty acid (SCFA), microbial acclimation of an activated sludge for directional conversion of other components of the SCFA into acetic acid, and analysis of the gas chromatograph for acetic acid are similar to embodiment 1. The method for continuous directional high-value biological conversion of the urban wet garbage open system is as follows: the wet garbage with a molar ratio of carbon to nitrogen being (18-35):1 was crushed at room temperature (a particle size (0.05-2) mm) and subjected to cooking and oil extraction, and a water phase was pumped into the hydrolysis reactor H with a temperature of 30° C., a pH value of 4 and a hydrolysis time of 12 hours; a hydrolyzed liquid was placed in the storage tank S1, and then transported through a pump to the SCFA-producing reactor R1 with a temperature of 20° C., a pH value of 6, a hydraulic retention time of 2 days, and a microbial retention time of 4 days; after solid-liquid separation of the settling tank C1, a microbial reflux amount of a precipitate was 40% of an inlet water amount of R1, a supernatant was placed in the storage tank S2 and then transported through a pump to the reactor R2 for directionally converting other components of SCFA into acetic acid (where operation conditions were a temperature of 20° C., a pH of 5, a hydraulic retention time of 1 day, and a microbial retention time of 2 days); an effluent of the R2 was subjected to solid-liquid separation of the settling tank C2, a microbial reflux amount of a precipitate was 30% of an inlet water amount of the R2, and a final supernatant was obtained as an acetic acid-rich liquid. According to analysis of the Agilent 6890 type gas chromatograph, an acetic acid concentration of the supernatant of the settling tank C2 was obtained as 4021 mg/L.

Embodiment 14

The methods for microbial acclimation of an activated sludge for conversion of organic components of the wet garbage into short-chain fatty acid (SCFA), microbial acclimation of an activated sludge for directional conversion of other components of the SCFA into acetic acid, and analysis of the gas chromatograph for acetic acid are similar to embodiment 1. The method for continuous directional high-value biological conversion of the urban wet garbage open system is as follows: the wet garbage with a molar ratio of carbon to nitrogen being (18-35):1 was crushed at room temperature (a particle size (0.05-2) mm) and subjected to cooking and oil extraction, and a water phase was pumped into the hydrolysis reactor H with a temperature of 30° C., a pH value of 5 and a hydrolysis time of 18 hours; a hydrolyzed liquid was placed in the storage tank S1, and then transported through a pump to the SCFA-producing reactor R1 with a temperature of 25° C., a pH value of 7, a hydraulic retention time of 2 days, and a microbial retention time of 4 days; after solid-liquid separation of the settling tank C1, a microbial reflux amount of a precipitate was 40% of an inlet water amount of R1, a supernatant was placed in the storage tank S2 and then transported through a pump to the reactor R2 for directionally converting other components of SCFA into acetic acid (where operation conditions were a temperature of 20° C., a pH of 5, a hydraulic retention time of 1 day, and a microbial retention time of 2.5 days); an effluent of the R2 was subjected to solid-liquid separation of the settling tank C2, a microbial reflux amount of a precipitate was 20% of an inlet water amount of the R2, and a final supernatant was obtained as an acetic acid-rich liquid. According to analysis of the Agilent 6890 type gas chromatograph, an acetic acid concentration of the supernatant of the settling tank C2 was obtained as 4192 mg/L.

Embodiment 15

The methods for microbial acclimation of an activated sludge for conversion of organic components of the wet garbage into short-chain fatty acid (SCFA), microbial acclimation of an activated sludge for directional conversion of other components of the SCFA into acetic acid, and analysis of the gas chromatograph for acetic acid are similar to embodiment 1. The method for continuous directional high-value biological conversion of the urban wet garbage open system is as follows: the wet garbage with a molar ratio of carbon to nitrogen being (18-35):1 was crushed at room temperature (a particle size (0.05-2) mm) and subjected to cooking and oil extraction, and a water phase was pumped into the hydrolysis reactor H with a temperature of 40° C., a pH value of 6 and a hydrolysis time of 24 hours; a hydrolyzed liquid was placed in the storage tank S1, and then transported through a pump to the SCFA-producing reactor R1 with a temperature of 35° C., a pH value of 7, a hydraulic retention time of 3 days, and a microbial retention time of 4 days; after solid-liquid separation of the settling tank C1, a microbial reflux amount of a precipitate was 40% of an inlet water amount of R1, a supernatant was placed in the storage tank S2 and then transported through a pump to the reactor R2 for directionally converting other components of SCFA into acetic acid (where operation conditions were a temperature of 25° C., a pH of 6, a hydraulic retention time of 2 days, and a microbial retention time of 3 days); an effluent of the R2 was subjected to solid-liquid separation of the settling tank C2, a microbial reflux amount of a precipitate was 40% of an inlet water amount of the R2, and a final supernatant was obtained as an acetic acid-rich liquid. According to analysis of the Agilent 6890 type gas chromatograph, an acetic acid concentration of the supernatant of the settling tank C2 was obtained as 4687 mg/L.

Embodiment 16

The methods for microbial acclimation of an activated sludge for conversion of organic components of the wet garbage into short-chain fatty acid (SCFA), microbial acclimation of an activated sludge for directional conversion of other components of the SCFA into acetic acid, and analysis of the gas chromatograph for acetic acid are similar to embodiment 1. The method for continuous directional high-value biological conversion of the urban wet garbage open system is as follows: the wet garbage with a molar ratio of carbon to nitrogen being (18-35):1 was crushed at room temperature (a particle size (0.05-2) mm) and subjected to cooking and oil extraction, and a water phase was pumped into the hydrolysis reactor H with a temperature of 60° C., a pH value of 7 and a hydrolysis time of 30 hours; a hydrolyzed liquid was placed in the storage tank S1, and then transported through a pump to the SCFA-producing reactor R1 with a temperature of 10° C., a pH value of 8, a hydraulic retention time of 4 days, and a microbial retention time of 5 days; after solid-liquid separation of the settling tank C1, a microbial reflux amount of a precipitate was 40% of an inlet water amount of R1, a supernatant was placed in the storage tank S2 and then transported through a pump to the reactor R2 for directionally converting other components of SCFA into acetic acid (where operation conditions were a temperature of 40° C., a pH of 7, a hydraulic retention time of 3 days, and a microbial retention time of 3 days); an effluent of the R2 was subjected to solid-liquid separation of the settling tank C2, a microbial reflux amount of a precipitate was 20% of an inlet water amount of the R2, and a final supernatant was obtained as an acetic acid-rich liquid. According to analysis of the Agilent 6890 type gas chromatograph, an acetic acid concentration of the supernatant of the settling tank C2 was obtained as 3665 mg/L.

Embodiment 17

The methods for microbial acclimation of an activated sludge for conversion of organic components of the wet garbage into short-chain fatty acid (SCFA), microbial acclimation of an activated sludge for directional conversion of other components of the SCFA into acetic acid, and analysis of the gas chromatograph for acetic acid are similar to embodiment 1. The method for continuous directional high-value biological conversion of the urban wet garbage open system is as follows: the wet garbage with a molar ratio of carbon to nitrogen being (18-35):1 was crushed at room temperature (a particle size (0.05-2) mm) and subjected to cooking and oil extraction, and a water phase was pumped into the hydrolysis reactor H with a temperature of 80° C., a pH value of 8 and a hydrolysis time of 36 hours; a hydrolyzed liquid was placed in the storage tank S1, and then transported through a pump to the SCFA-producing reactor R1 with a temperature of 50° C., a pH value of 8, a hydraulic retention time of 5 days, and a microbial retention time of 6 days; after solid-liquid separation of the settling tank C1, a microbial reflux amount of a precipitate was 40% of an inlet water amount of R1, a supernatant was placed in the storage tank S2 and then transported through a pump to the reactor R2 for directionally converting other components of SCFA into acetic acid (where operation conditions were a temperature of 50° C., a pH of 8, a hydraulic retention time of 4 days, and a microbial retention time of 4 days); an effluent of the R2 was subjected to solid-liquid separation of the settling tank C2, a microbial reflux amount of a precipitate was 60% of an inlet water amount of the R2, and a final supernatant was obtained as an acetic acid-rich liquid. According to analysis of the Agilent 6890 type gas chromatograph, an acetic acid concentration of the supernatant of the settling tank C2 was obtained as 4942 mg/L.

Embodiment 18

The methods for microbial acclimation of an activated sludge for conversion of organic components of the wet garbage into short-chain fatty acid (SCFA), microbial acclimation of an activated sludge for directional conversion of other components of the SCFA into acetic acid, and analysis of the gas chromatograph for acetic acid are similar to embodiment 1. The method for continuous directional high-value biological conversion of the urban wet garbage open system is as follows: the wet garbage with a molar ratio of carbon to nitrogen being (18-35):1 was crushed at room temperature (a particle size (0.05-2) mm) and subjected to cooking and oil extraction, and a water phase was pumped into the hydrolysis reactor H with a temperature of 90° C., a pH value of 11 and a hydrolysis time of 48 hours; a hydrolyzed liquid was placed in the storage tank S1, and then transported through a pump to the SCFA-producing reactor R1 with a temperature of 60° C., a pH value of 9, a hydraulic retention time of 7 days, and a microbial retention time of 8 days; after solid-liquid separation of the settling tank C1, a microbial reflux amount of a precipitate was 40% of an inlet water amount of R1, a supernatant was placed in the storage tank S2 and then transported through a pump to the reactor R2 for directionally converting other components of SCFA into acetic acid (where operation conditions were a temperature of 60° C., a pH of 9, a hydraulic retention time of 5 days, and a microbial retention time of 8 days); an effluent of the R2 was subjected to solid-liquid separation of the settling tank C2, a microbial reflux amount of a precipitate was 45% of an inlet water amount of the R2, and a final supernatant was obtained as an acetic acid-rich liquid. According to analysis of the Agilent 6890 type gas chromatograph, an acetic acid concentration of the supernatant of the settling tank C2 was obtained as 5186 mg/L.

Embodiment 19

The methods for microbial acclimation of an activated sludge for conversion of organic components of the wet garbage into short-chain fatty acid (SCFA), microbial acclimation of an activated sludge for directional conversion of other components of the SCFA into acetic acid, and analysis of the gas chromatograph for acetic acid are similar to embodiment 1. The method for continuous directional high-value biological conversion of the urban wet garbage open system is as follows: the wet garbage with a molar ratio of carbon to nitrogen being (18-35):1 was crushed at room temperature (a particle size (0.05-2) mm) and subjected to cooking and oil extraction, and a water phase was pumped into the hydrolysis reactor H with a temperature of 100° C., a pH value of 12 and a hydrolysis time of 60 hours; a hydrolyzed liquid was placed in the storage tank S1, and then transported through a pump to the SCFA-producing reactor R1 with a temperature of 70° C., a pH value of 10, a hydraulic retention time of 8 days, and a microbial retention time of 10 days; after solid-liquid separation of the settling tank C1, a microbial reflux amount of a precipitate was 40% of an inlet water amount of R1, a supernatant was placed in the storage tank S2 and then transported through a pump to the reactor R2 for directionally converting other components of SCFA into acetic acid (where operation conditions were a temperature of 20° C., a pH of 12, a hydraulic retention time of 6 days, and a microbial retention time of 3 days); an effluent of the R2 was subjected to solid-liquid separation of the settling tank C2, a microbial reflux amount of a precipitate was 80% of an inlet water amount of the R2, and a final supernatant was obtained as an acetic acid-rich liquid. According to analysis of the Agilent 6890 type gas chromatograph, an acetic acid concentration of the supernatant of the settling tank C2 was obtained as 4396 mg/L.

Embodiment 20

The methods for microbial acclimation of an activated sludge for conversion of organic components of the wet garbage into short-chain fatty acid (SCFA), microbial acclimation of an activated sludge for directional conversion of other components of the SCFA into acetic acid, and analysis of the gas chromatograph for acetic acid are similar to embodiment 1. The method for continuous directional high-value biological conversion of the urban wet garbage open system is as follows: the wet garbage with a molar ratio of carbon to nitrogen being (18-35):1 was crushed at room temperature (a particle size (0.05-2) mm) and subjected to cooking and oil extraction, and a water phase was pumped into the hydrolysis reactor H with a temperature of 30° C., a pH value of 9 and a hydrolysis time of 120 hours; a hydrolyzed liquid was placed in the storage tank S1, and then transported through a pump to the SCFA-producing reactor R1 with a temperature of 40° C., a pH value of 7, a hydraulic retention time of 5 days, and a microbial retention time of 4 days; after solid-liquid separation of the settling tank C1, a microbial reflux amount of a precipitate was 40% of an inlet water amount of R1, a supernatant was placed in the storage tank S2 and then transported through a pump to the reactor R2 for directionally converting other components of SCFA into acetic acid (where operation conditions were a temperature of 80° C., a pH of 6, a hydraulic retention time of 3 days, and a microbial retention time of 13 days); an effluent of the R2 was subjected to solid-liquid separation of the settling tank C2, a microbial reflux amount of a precipitate was 100% of an inlet water amount of the R2, and a final supernatant was obtained as an acetic acid-rich liquid. According to analysis of the Agilent 6890 type gas chromatograph, an acetic acid concentration of the supernatant of the settling tank C2 was obtained as 4561 mg/L.

Embodiment 21

The methods for microbial acclimation of an activated sludge for conversion of organic components of the wet garbage into short-chain fatty acid (SCFA), microbial acclimation of an activated sludge for directional conversion of other components of the SCFA into acetic acid, and analysis of the gas chromatograph for acetic acid are similar to embodiment 1. The method for continuous directional high-value biological conversion of the urban wet garbage open system is as follows: the wet garbage with a molar ratio of carbon to nitrogen being (18-35):1 was crushed at room temperature (a particle size (0.05-2) mm) and subjected to cooking and oil extraction, and a water phase was pumped into the hydrolysis reactor H with a temperature of 40° C., a pH value of 11 and a hydrolysis time of 60 hours; a hydrolyzed liquid was placed in the storage tank S1, and then transported through a pump to the SCFA-producing reactor R1 with a temperature of 25° C., a pH value of 8, a hydraulic retention time of 5 days, and a microbial retention time of 6 days; after solid-liquid separation of the settling tank C1, a microbial reflux amount of a precipitate was 40% of an inlet water amount of R1, a supernatant was placed in the storage tank S2 and then transported through a pump to the reactor R2 for directionally converting other components of SCFA into acetic acid (where operation conditions were a temperature of 25° C., a pH of 9, a hydraulic retention time of 3 days, and a microbial retention time of 8 days); an effluent of the R2 was subjected to solid-liquid separation of the settling tank C2, a microbial reflux amount of a precipitate was 50% of an inlet water amount of the R2, and a final supernatant was obtained as an acetic acid-rich liquid. According to analysis of the Agilent 6890 type gas chromatograph, an acetic acid concentration of the supernatant of the settling tank C2 was obtained as 5414 mg/L.

Embodiment 22

The methods for microbial acclimation of an activated sludge for conversion of organic components of the wet garbage into short-chain fatty acid (SCFA), microbial acclimation of an activated sludge for directional conversion of other components of the SCFA into acetic acid, and analysis of the gas chromatograph for acetic acid are similar to embodiment 1. The method for continuous directional high-value biological conversion of the urban wet garbage open system is as follows: the wet garbage with a molar ratio of carbon to nitrogen being (18-35):1 was crushed at room temperature (a particle size (0.05-2) mm) and subjected to cooking and oil extraction, and a water phase was pumped into the hydrolysis reactor H with a temperature of 20° C., a pH value of 3 and a hydrolysis time of 5 hours; a hydrolyzed liquid was placed in the storage tank S1, and then transported through a pump to the SCFA-producing reactor R1 with a temperature of 10° C., a pH value of 5, a hydraulic retention time of 1 day, and a microbial retention time of 3 days; after solid-liquid separation of the settling tank C1, a microbial reflux amount of a precipitate was 60% of an inlet water amount of R1, a supernatant was placed in the storage tank S2 and then transported through a pump to the reactor R2 for directionally converting other components of SCFA into acetic acid (where operation conditions were a temperature of 10° C., a pH of 4, a hydraulic retention time of 0.5 days, and a microbial retention time of 1 day); an effluent of the R2 was subjected to solid-liquid separation of the settling tank C2, a microbial reflux amount of a precipitate was 20% of an inlet water amount of the R2, and a final supernatant was obtained as an acetic acid-rich liquid. According to analysis of the Agilent 6890 type gas chromatograph, an acetic acid concentration of the supernatant of the settling tank C2 was obtained as 3552 mg/L.

Embodiment 23

The methods for microbial acclimation of an activated sludge for conversion of organic components of the wet garbage into short-chain fatty acid (SCFA), microbial acclimation of an activated sludge for directional conversion of other components of the SCFA into acetic acid, and analysis of the gas chromatograph for acetic acid are similar to embodiment 1. The method for continuous directional high-value biological conversion of the urban wet garbage open system is as follows: the wet garbage with a molar ratio of carbon to nitrogen being (18-35):1 was crushed at room temperature (a particle size (0.05-2) mm) and subjected to cooking and oil extraction, and a water phase was pumped into the hydrolysis reactor H with a temperature of 30° C., a pH value of 4 and a hydrolysis time of 12 hours; a hydrolyzed liquid was placed in the storage tank S1, and then transported through a pump to the SCFA-producing reactor R1 with a temperature of 20° C., a pH value of 6, a hydraulic retention time of 2 days, and a microbial retention time of 4 days; after solid-liquid separation of the settling tank C1, a microbial reflux amount of a precipitate was 60% of an inlet water amount of R1, a supernatant was placed in the storage tank S2 and then transported through a pump to the reactor R2 for directionally converting other components of SCFA into acetic acid (where operation conditions were a temperature of 20° C., a pH of 5, a hydraulic retention time of 1 day, and a microbial retention time of 2 days); an effluent of the R2 was subjected to solid-liquid separation of the settling tank C2, a microbial reflux amount of a precipitate was 30% of an inlet water amount of the R2, and a final supernatant was obtained as an acetic acid-rich liquid. According to analysis of the Agilent 6890 type gas chromatograph, an acetic acid concentration of the supernatant of the settling tank C2 was obtained as 3802 mg/L.

Embodiment 24

The methods for microbial acclimation of an activated sludge for conversion of organic components of the wet garbage into short-chain fatty acid (SCFA), microbial acclimation of an activated sludge for directional conversion of other components of the SCFA into acetic acid, and analysis of the gas chromatograph for acetic acid are similar to embodiment 1. The method for continuous directional high-value biological conversion of the urban wet garbage open system is as follows: the wet garbage with a molar ratio of carbon to nitrogen being (18-35):1 was crushed at room temperature (a particle size (0.05-2) mm) and subjected to cooking and oil extraction, and a water phase was pumped into the hydrolysis reactor H with a temperature of 30° C., a pH value of 5 and a hydrolysis time of 18 hours; a hydrolyzed liquid was placed in the storage tank S1, and then transported through a pump to the SCFA-producing reactor R1 with a temperature of 25° C., a pH value of 7, a hydraulic retention time of 2 days, and a microbial retention time of 4 days; after solid-liquid separation of the settling tank C1, a microbial reflux amount of a precipitate was 60% of an inlet water amount of R1, a supernatant was placed in the storage tank S2 and then transported through a pump to the reactor R2 for directionally converting other components of SCFA into acetic acid (where operation conditions were a temperature of 20° C., a pH of 5, a hydraulic retention time of 1 day, and a microbial retention time of 2.5 days); an effluent of the R2 was subjected to solid-liquid separation of the settling tank C2, a microbial reflux amount of a precipitate was 20% of an inlet water amount of the R2, and a final supernatant was obtained as an acetic acid-rich liquid. According to analysis of the Agilent 6890 type gas chromatograph, an acetic acid concentration of the supernatant of the settling tank C2 was obtained as 3998 mg/L.

Embodiment 25

The methods for microbial acclimation of an activated sludge for conversion of organic components of the wet garbage into short-chain fatty acid (SCFA), microbial acclimation of an activated sludge for directional conversion of other components of the SCFA into acetic acid, and analysis of the gas chromatograph for acetic acid are similar to embodiment 1. The method for continuous directional high-value biological conversion of the urban wet garbage open system is as follows: the wet garbage with a molar ratio of carbon to nitrogen being (18-35):1 was crushed at room temperature (a particle size (0.05-2) mm) and subjected to cooking and oil extraction, and a water phase was pumped into the hydrolysis reactor H with a temperature of 40° C., a pH value of 6 and a hydrolysis time of 24 hours; a hydrolyzed liquid was placed in the storage tank S1, and then transported through a pump to the SCFA-producing reactor R1 with a temperature of 35° C., a pH value of 7, a hydraulic retention time of 3 days, and a microbial retention time of 4 days; after solid-liquid separation of the settling tank C1, a microbial reflux amount of a precipitate was 60% of an inlet water amount of R1, a supernatant was placed in the storage tank S2 and then transported through a pump to the reactor R2 for directionally converting other components of SCFA into acetic acid (where operation conditions were a temperature of 25° C., a pH of 6, a hydraulic retention time of 2 days, and a microbial retention time of 3 days); an effluent of the R2 was subjected to solid-liquid separation of the settling tank C2, a microbial reflux amount of a precipitate was 40% of an inlet water amount of the R2, and a final supernatant was obtained as an acetic acid-rich liquid. According to analysis of the Agilent 6890 type gas chromatograph, an acetic acid concentration of the supernatant of the settling tank C2 was obtained as 4468 mg/L.

Embodiment 26

The methods for microbial acclimation of an activated sludge for conversion of organic components of the wet garbage into short-chain fatty acid (SCFA), microbial acclimation of an activated sludge for directional conversion of other components of the SCFA into acetic acid, and analysis of the gas chromatograph for acetic acid are similar to embodiment 1. The method for continuous directional high-value biological conversion of the urban wet garbage open system is as follows: the wet garbage with a molar ratio of carbon to nitrogen being (18-35):1 was crushed at room temperature (a particle size (0.05-2) mm) and subjected to cooking and oil extraction, and a water phase was pumped into the hydrolysis reactor H with a temperature of 60° C., a pH value of 7 and a hydrolysis time of 30 hours; a hydrolyzed liquid was placed in the storage tank S1, and then transported through a pump to the SCFA-producing reactor R1 with a temperature of 10° C., a pH value of 8, a hydraulic retention time of 4 days, and a microbial retention time of 5 days; after solid-liquid separation of the settling tank C1, a microbial reflux amount of a precipitate was 60% of an inlet water amount of R1, a supernatant was placed in the storage tank S2 and then transported through a pump to the reactor R2 for directionally converting other components of SCFA into acetic acid (where operation conditions were a temperature of 40° C., a pH of 7, a hydraulic retention time of 3 days, and a microbial retention time of 3 days); an effluent of the R2 was subjected to solid-liquid separation of the settling tank C2, a microbial reflux amount of a precipitate was 20% of an inlet water amount of the R2, and a final supernatant was obtained as an acetic acid-rich liquid. According to analysis of the Agilent 6890 type gas chromatograph, an acetic acid concentration of the supernatant of the settling tank C2 was obtained as 3444 mg/L.

In conclusion, in contrast with a closed aseptic operation system or a system where pure microbes are present, the present invention performs two stages of anaerobic fermentations to firstly convert organic components of the wet garbage continuously into short-chain fatty acid, and then continuously and directionally convert other components of short-chain fatty acid into acetic acid, so as to realize continuous directional high-value biological conversion of the urban wet garbage in an open system without adding pure microbes and a large amount of chemicals. In this way, the problem that products are difficult to directionally synthesize due to presence of multiple types of microbes in the system when organic matters perform anaerobic conversion in the open system is solved, which provides a new technology for efficient disposal and high-value directional conversion of the wet garbage after urban garbage classification.

Furthermore, it should be understood that one or more method steps in the present invention do not preclude presence of other method steps after or before the step combination nor preclude interposition of other method steps between the steps mentioned herein unless otherwise stated. It should also be understood that unless otherwise stated, the numerals of these method steps are a convenient tool for discriminating various method steps rather than limiting the sequence of various method steps or defining the practice scope of the present invention, and any change or adjustment to their relative relationship shall also be regarded as within the practice scope of the present invention unless technical contents are substantially changed.

The above embodiments are used only to illustratively explain the principle and efficacy of the present invention rather than limit the present invention. Those skilled in the art may make modifications or changes to the above embodiments within the spirit and scope of the present invention. Therefore, all equivalent modifications or changes made by those having common knowledge in the prior art without departing from the spirit and technical idea of the present invention shall all fall within the scope of protection of the present invention.

What is claimed is:

1. A method of enhancing continuous directional biological conversion of an urban wet garbage open system, comprising the following steps:
   (1) wet garbage crushing: crushing a wet garbage and then adding tap water to perform cooking and oil extraction, and then pumping a water phase of the crushed wet garbage into a hydrolysis reactor H;
   (2) hydrolysis: hydrolyzing the water phase of the crushed wet garbage in the hydrolysis reactor H to obtain a hydrolysate and then pumping the obtained hydrolysate into a storage tank S1;
   (3) microbial acclimation of an activated sludge for converting organic components of the wet garbage into short-chain fatty acid: adding an urban sewage into a microbial acclimation reactor A1, and then adding a wastewater plant residual sludge and the hydrolysate respectively to enable a starting sludge concentration to be 8000 mg/L and a starting hydrolysate chemical oxygen demand (COD) to be 1000 mg/L in the microbial acclimation reactor A1, adjusting a pH of the mixture in the microbial acclimation reactor A1 to 8, and performing anaerobic stirring and acclimation for the mixture at a temperature of 25° C.; when a total amount of short-chain fatty acid in the reactor does not change obviously any longer, taking the sludge as a seeding sludge for converting organic components of the wet garbage into short-chain fatty acid (SCFA) efficiently;

(4) continuous conversion of organic components of the wet garbage into short-chain fatty acid: pumping the hydrolysate in the storage tank S1 and 500 mL of the seeding sludge acclimatized at step (3) into an SCFA-producing reactor R1 to enable a sludge concentration in the SCFA-producing reactor R1 to be 2000 mg/L and controlling a temperature, a pH value, a hydraulic retention time, and a microbial retention time to fully convert the organic components of the wet garbage into a mixture rich in short-chain fatty acid;

(5) separation and microbial reflux of short-chain fatty acid: introducing the generated mixture rich in short-chain fatty acid into a settling tank C1 for solid-liquid separation, introducing a supernatant obtained through solid-liquid separation into a storage tank S2, and refluxing a part of a precipitate obtained through solid-liquid separation to the SCFA-producing reactor R1;

(6) microbial acclimation of an activated sludge for directional conversion of other components of short-chain fatty acid into acetic acid: adding an urban sewage, a wastewater plant residual sludge and the liquid in the storage tank S2 to another microbial acclimation reactor A2 to enable a sludge concentration to be 8600 mg/L and a short-chain fatty acid COD to be 1000 mg/L in the microbial acclimation reactor A2, adjusting a pH to 9, and performing anaerobic stirring and acclimation at a temperature of 25° C. to enable propanoic acid, butyric acid and pentanoic acid in the short-chain fatty acid obtained by converting the wet garbage to be directionally converted into acetic acid;

(7) continuous directional conversion of other components of short-chain fatty acid into acetic acid: pumping the liquid in the storage tank S2 and 800 ml of the sludge acclimatized at step (6) to a reactor R2 for converting other components of SCFA into acetic acid to enable a sludge concentration to be 9000 mg/L in the reactor R2 for converting other components into acetic acid, and controlling a temperature, a pH value, a hydraulic retention time, and a microbial retention time to enable propanoic acid, butyric acid and pentanoic acid in the SCFA produced at step (4) to be directionally converted into acetic acid;

(8) acetic acid separation and microbial reflux: introducing an acetic acid-rich mixture produced by the reactor R2 for converting other components of SCFA into acetic acid into a settling tank C2 for solid-liquid separation, obtaining a supernatant as an acetic acid-rich liquid through solid-liquid separation and refluxing a part of a precipitate obtained through solid-liquid separation to the reactor R2;

wherein the steps (1)-(8) are conducted in an open system;

wherein no pure microbe is added to the crushed wet garbage.

2. The method according to claim 1, wherein a molar ratio of carbon to nitrogen of the wet garbage is 18-35:1, and a particle size of the crushed wet garbage is 0.05-2 mm.

3. The method according to claim 1, wherein working conditions of the hydrolysis reactor H are temperature 20-100° C., pH value 3-12 and time 5-120 hours.

4. The method according to claim 1, wherein the working conditions of the hydrolysis reactor H are temperature 40° C., pH value 11 and time 60 hours.

5. The method according to claim 1, wherein conditions for continuously converting the organic components of the wet garbage into short-chain fatty acid at step (4) are: temperature 10-70° C., pH value 5-10, hydraulic retention time 1-8 days, microbial mean retention time 3-10 days.

6. The method according to claim 1, wherein the conditions for continuously converting the organic components of the wet garbage into short-chain fatty acid at step (4) are: temperature 25° C., pH value 8, hydraulic retention time 5 days, microbial mean retention time 6 days.

7. The method according to claim 1, wherein the settling tank C1 is a vertical flow settling tank with a depth-diameter ratio of 2.5 and a round hopper tilt angle of 55 degrees, and a microbial reflux amount at step (5) is 0-60% of an inlet water amount of the SCFA-producing reactor R1.

8. The method according to claim 1, wherein conditions for continuous directional conversion of other components of short-chain fatty acid into acetic acid at step (6) are: temperature 10-80° C., pH value 4-12, hydraulic retention time 0.5-6 days, microbial mean retention time 1-13 days.

9. The method according to claim 1, wherein the conditions for continuous directional conversion of other components of short-chain fatty acid into acetic acid at step (6) are: temperature 25° C., pH value 9, hydraulic retention time 3 days, microbial mean retention time 8 days.

10. The method according to claim 1, wherein the settling tank C2 is a vertical flow settling tank with a depth-diameter ratio of 3 and a round hopper tilt angle of 60 degrees, and a microbial reflux amount at step (8) is 0-100% of an inlet water amount of the reactor R2 for converting other components of SCFA into acetic acid.

* * * * *